US006656227B2

United States Patent
Levin

(10) Patent No.: US 6,656,227 B2
(45) Date of Patent: Dec. 2, 2003

(54) PROSTHESIS FOR INTERNAL PERITONEAL DIALYSIS AND METHOD OF PROVIDING PERITONEAL DIALYSIS

(76) Inventor: John M. Levin, 819 Chauncey Rd., Narberth, PA (US) 19072

( * ) Notice: Subject to any disclaimer, the term of this patent is extended or adjusted under 35 U.S.C. 154(b) by 78 days.

(21) Appl. No.: 09/833,286

(22) Filed: Apr. 12, 2001

(65) Prior Publication Data

US 2002/0107467 A1 Aug. 8, 2002

Related U.S. Application Data

(63) Continuation-in-part of application No. 09/693,591, filed on Oct. 20, 2000.

(51) Int. Cl.[7] .......................... A61F 2/04; A61M 37/00; A61M 1/00
(52) U.S. Cl. ...................................... 623/23.65; 604/29
(58) Field of Search .......................... 623/23.64–23.66; 604/8–9, 28–29, 131, 890.1, 4.01, 5.01–5.04, 6.01–6.09, 93.01, 288.01, 288.04

(56) References Cited

U.S. PATENT DOCUMENTS

| 3,579,441 A | | 5/1971 | Brown |
| 3,707,967 A | * | 1/1973 | Kitrilakis et al. .............. 604/29 |
| 4,368,737 A | * | 1/1983 | Ash ........................... 604/175 |
| 4,437,856 A | | 3/1984 | Valli |
| 4,586,920 A | | 5/1986 | Peabody |
| 4,655,762 A | * | 4/1987 | Rogers ........................ 604/403 |
| 4,681,564 A | * | 7/1987 | Landreneau ................ 604/128 |
| 4,922,926 A | * | 5/1990 | Hirschberg et al. ......... 607/120 |
| 5,037,385 A | * | 8/1991 | O'Byrne ...................... 604/28 |
| 5,254,084 A | * | 10/1993 | Geary .......................... 604/29 |
| 5,512,048 A | * | 4/1996 | Slettenmark ........... 604/288.01 |
| 5,813,410 A | | 9/1998 | Levin |
| 5,980,480 A | | 11/1999 | Rubenstein et al. |
| 5,980,481 A | | 11/1999 | Gorsuch |
| 6,132,415 A | * | 10/2000 | Finch et al. ................. 604/502 |
| 6,569,130 B1 | * | 5/2003 | Levin ..................... 604/288.01 |
| 2003/0036718 A1 | * | 2/2003 | Connelly et al. .......... 604/5.01 |

FOREIGN PATENT DOCUMENTS

EP          0 366 389        5/1990

OTHER PUBLICATIONS

EP Search Report from corresponding International Application No. PCT/US01/46239, mailed Aug. 26, 2002.

* cited by examiner

Primary Examiner—Corrine McDermott
Assistant Examiner—Alvin Stewart
(74) Attorney, Agent, or Firm—Caesar, Rivise, Bernstein, Cohen & Pokotilow, Ltd.

(57) ABSTRACT

Continuous internal peritoneal dialysis prosthesis and method employing an abdominal sac adapted to be retained in the abdominal region of a patient's body and including dialysate therein for permitting unconcentrated urine within the peritoneal region to pass through a semi-permeable membrane wall of the abdominal sac. The unconcentrated urine within the abdominal sac is directed through a section of the patient's bowel and is communicated with the internal wall of the bowel to thereby concentrate the urine. The concentrated urine is then directed into the urinary bladder for subsequent excretion from the patient's body. In the preferred prosthesis and method of this invention the normal breathing pattern of the patient is employed to assist in the circulation of the unconcentrated urine from the abdominal sac into and through the section of the patient's bowel. In alternative embodiments, the dialysate may be contained within the abdominal sac, contained within the prosthesis, or allowed to directly contact the peritoneum. Moreover, in a further embodiment, an abdominal sac is omitted and the peritoneal region of the body retains the dialysate and unconcentrated urine.

17 Claims, 6 Drawing Sheets

PROSTHESIS FOR INTERNAL PERITONEAL DIALYSIS AND METHOD OF PROVIDING PERITONEAL DIALYSIS

SPECIFICATION

This application is a Continuation-In-Part of U.S. patent application Ser. No. 09/693,591, filed Oct. 20, 2000, now pending and entitled "Prosthesis for Continuous Internal Peritoneal Dialysis and Continuous Method of Providing Peritoneal Dialysis."

FIELD OF THE INVENTION

This invention relates to generally to prosthesis for continuous internal peritoneal dialysis and a continuous method of carrying out peritoneal dialysis. More specifically, this invention relates to artificial kidneys, and more specifically to artificial kidneys implantable within a person's body with the intent that the patient be free from dialysis and transplantation. The artificial kidneys of this invention employ the normal operation of the person's body (i.e., breathing cycle of the person) to cause the flow of fluid within the prosthesis for the removal of toxic substances or other fluids from the person's body. For the treatment of edema states that are refractory to treatment with diuretics the dialysate can be a selected hypertonic solution for removing excess fluids; principally water.

BACKGROUND OF THE INVENTION

The dialysis art is a highly developed one; providing a variety of teachings for dialyzing a patient.

In accordance with a related dialysis procedure (e.g., hemodialysis) for purifying blood in a patient experiencing kidney failure, the contaminated blood is directed from a blood vessel of the patient's arm through a dialyzing membrane located extracorporeally of the body, in which the blood gives up its impurities to the dialyzing fluid. The purified blood is then directed back into the patient's body through another blood vessel. A representative disclosure of a system for use in purifying arterial blood and providing a venous return is disclosed in U.S. Pat. No. 3,579,441, issued to Brown.

The dialysis art also suggests the use of related peritoneal dialysis systems, wherein a dialysate is introduced directly into the abdomen of the patient and functions to receive impurities from the blood at the abdominal capillaries, and then is mechanically removed from the body. Representative peritoneal dialysis systems of this type are disclosed in U.S. Pat. Nos. 4,681,564 (Landreneau); 4,655,762 (Rogers); 4,586,920 (Peabody) and 4,437,856 (Valli).

All of the related art systems known to applicants suffer from one or more disadvantages. For example, a number of prior art systems require that the patient be connected, e.g., "hooked-up", to a dialysis machine. This renders the patient immobile during treatment, is expensive to administer, and subjects the patient to a high risk of infection, and even death. Patients are protein restricted, because protein yields toxic degradation products (e.g., nitrogenous wastes) largely responsible for uremia, the state of being in kidney failure. Toxic levels of potassium may also result from the treatment. Moreover, chronic contact of the peritoneum with hypertonic dialysate solutions often creates chronic peritonitis, which is a painful, dangerous condition that interferes with the peritoneal dialysis process.

The absorption of dialysate into the bloodstream interferes with the peritoneum dialysate's ability to do its job of pulling in fluids. Therefore, peritoneal dialysis relies physiologically on the fact that the dialysis fluid in the abdominal cavity is more viscous or thicker than blood. In other words, the dialysis fluid has a higher osmolality or chemical potential than the bloodstream. This difference in potential causes water and other molecules known to those skilled in the art to diffuse into the abdomen via the semi-permeable membranes of the peritoneum and mesenteric parietes which line the abdominal cavity.

Additionally, all previous modes of dialysis have been essentially intermittent, rather than continuous; resulting in a variety of disturbances to the body's equilibrium. Patients become either over-hydrated or under-hydrated due to the intermittent process of adding and removing fluids. The systems can not maintain proper blood volume and chemical balance beyond the few hours following the treatment. The treatments sap the patient's energy and sense of well-being, making the patient look and feel chronically ill, and critically affecting the patient's lifestyle, happiness and longevity.

With respect to transplantation, the high cost and risks are well known. A match for the patient must be found, which may take years. If a kidney is found, and the patient is still strong enough to receive it, then there is no guarantee that the kidney will be accepted. The patient's immune system may recognize a kidney transplanted from another as foreign matter and act to combat and reject this perceived invasion. Anti-rejection medication, such as azathioprine, cyclosporine and steroids help to prevent rejection. However, anti-rejection medicines have a large number of side effects. If rejection occurs, treatment is available to possibly reverse the episode, but at the cost of more medication and side effects. With kidney transplantation, about one third of the patients do very well, about one third remain chronically ill, and about one third of the patients die within five years.

A need clearly exists for an artificial kidney, or prosthesis, that is lower in cost than existing systems, that can be utilized with a minimum of risk to the patient, that provides greater freedom of movement for the patient and that allows for the continuous formation of urine as in a normal functioning kidney. Therefore, it would be beneficial to provide a continuous internal peritoneal dialysis prosthesis and method. It would also be beneficial to provide a continuous internal peritoneal dialysis prosthesis and method which employs the normal breathing pattern of the patient to affect the dialysis operation, which is simple in operation and requires relatively few moving parts.

To applicant's knowledge, prior to this invention, there has been no artificial kidney that is implantable in the body to provide any of the functions normally provided by a healthy kidney. It is to such artificial kidneys that the present invention is directed.

SUMMARY OF THE INVENTION

The above and other objects of this invention are achieved, in whole or in part, by a continuous internal peritoneal dialysis prosthesis and method employing an abdominal sac including a dialysate therein, said abdominal sac being adapted to be retained in the abdominal region of a person's body for receiving unconcentrated urine through the walls of the sac without permitting dialysate to exit from the sac through the walls. The abdominal sac communicates the unconcentrated urine through a section of the patient's bowel via a conduit that extends through the section of bowel. A region of the conduit within the section of the patient's bowel includes apertures therein for communicating the unconcentrated urine in the conduit with walls of the section of bowel; thereby employing the natural function of the bowel to concentrate the urine. The prosthesis also includes a connector that is adopted for directing concentrated urine from the bowel to the urinary bladder.

In one preferred prosthesis of this invention, the conduit includes a first conduit section and a second conduit section. The first section communicates the abdominal sac with a pouch adopted to be placed in the thoracic region of the patient's body. The second conduit section communicates with the pouch and extends through the section of the patient's bowel. The second conduit section includes apertures for controlling the rate of flow of unconcentrated urine through the bowel so as to provide adequate time for the bowel to provide its required urine concentrating function, and to direct said concentrated urine to the urinary bladder for ultimate excretion by the body.

In the most preferred embodiment of this invention, the distal end of the second conduit communicates with the dialysis sac.

In the most preferred embodiment of this invention, the connecting means to the urinary bladder includes the right ureter connecting the bowel to the urinary bladder and most preferably, the connecting means is through the appendix or cecum.

The continuous internal peritoneal dialysis method of this invention includes the steps of providing an abdominal sac in the peritoneal region of a patient, said sac including a dialysate therein and a wall adopted for permitting unconcentrated urine to pass therethrough into the dialysate in the sac while preventing the escape of dialysate from the sac; directing the unconcentrated urine therein out of the abdominal sac and through a section of a patient's bowel in which the urine is concentrated, and then directing the concentrated urine into the urinary bladder for subsequent excretion from the human body in a conventional, or normal manner.

In accordance with the preferred method of this invention, a portion of the urine that is not concentrated within the bowel is caused to flow back to the abdominal sac.

In the most preferred method of this invention, the step of directing the unconcentrated urine through the section of bowel is carried out by first directing the unconcentrated urine into a thoracic pouch located in the thoracic region of a patient, the abdominal sac and thoracic pouch being flexible.

Most preferably, the process employs the normal breathing activity of the patient to continuously direct the unconcentrated urine from the abdominal sac to the thoracic pouch and then through the section of bowel.

In another preferred embodiment, a prosthesis for continuous internal peritoneal dialysis comprises a thoracic pouch and first and second conduits. The first conduit communications unconcentrated urine and dialysate from the abdominal region of a patient's body through the patient's diaphragm to the thoracic region of the body. The thoracic pouch is adapted to be retained in the thoracic region of the patient's body, and communicates with the first conduit to receive the unconcentrated urine and dialysate from the abdominal region. The second conduit extends from the thoracic pouch through the patient's diaphragm and a section of the patient's bowel. The second conduit communicates the unconcentrated urine and dialysate from the thoracic pouch with walls of the section of the bowel for concentrating the urine within the section of bowel. The section of bowel includes an exit port for directing the concentrated urine from the section of bowel to the urinary bladder of the patient.

In another preferred embodiment, an abdominal sac for internal peritoneal dialysis includes a semi-permeable membrane wall and is arranged for having a dialysate therein. The sac is adapted to be retained in the abdominal region of a patient's body for receiving unconcentrated urine through the semi-permeable membrane wall without permitting the diaysate to exit from the abdominal sac through the wall. The dialysate asserts a chemical potential to draw in the unconcentrated urine by osmotic pressure through the semi-permeable membrane wall. The sac includes an extension expanding into a section of the patient's bowel. The extension includes the semi-permeable membrane wall for permitting the received unconcentrated urine to exit into the section of bowel for concentrating the urine. The section of bowel includes an exit port for directing the concentrated urine from the section of bowel into the urinary bladder of the patient.

Further scope of applicability of the present invention will become apparent from the description given hereinafter. However, it should be understood that the detailed description and specific examples, while indicating preferred embodiments of the invention, are given by way of illustration only, since the invention will become apparent to those skilled in the art from this detailed description.

BRIEF DESCRIPTION OF THE DRAWINGS

The invention will be described in conjunction with the following drawings in which like reference numbers designate like elements, and wherein.

DETAILED DESCRIPTION OF THE INVENTION

Figure 1:
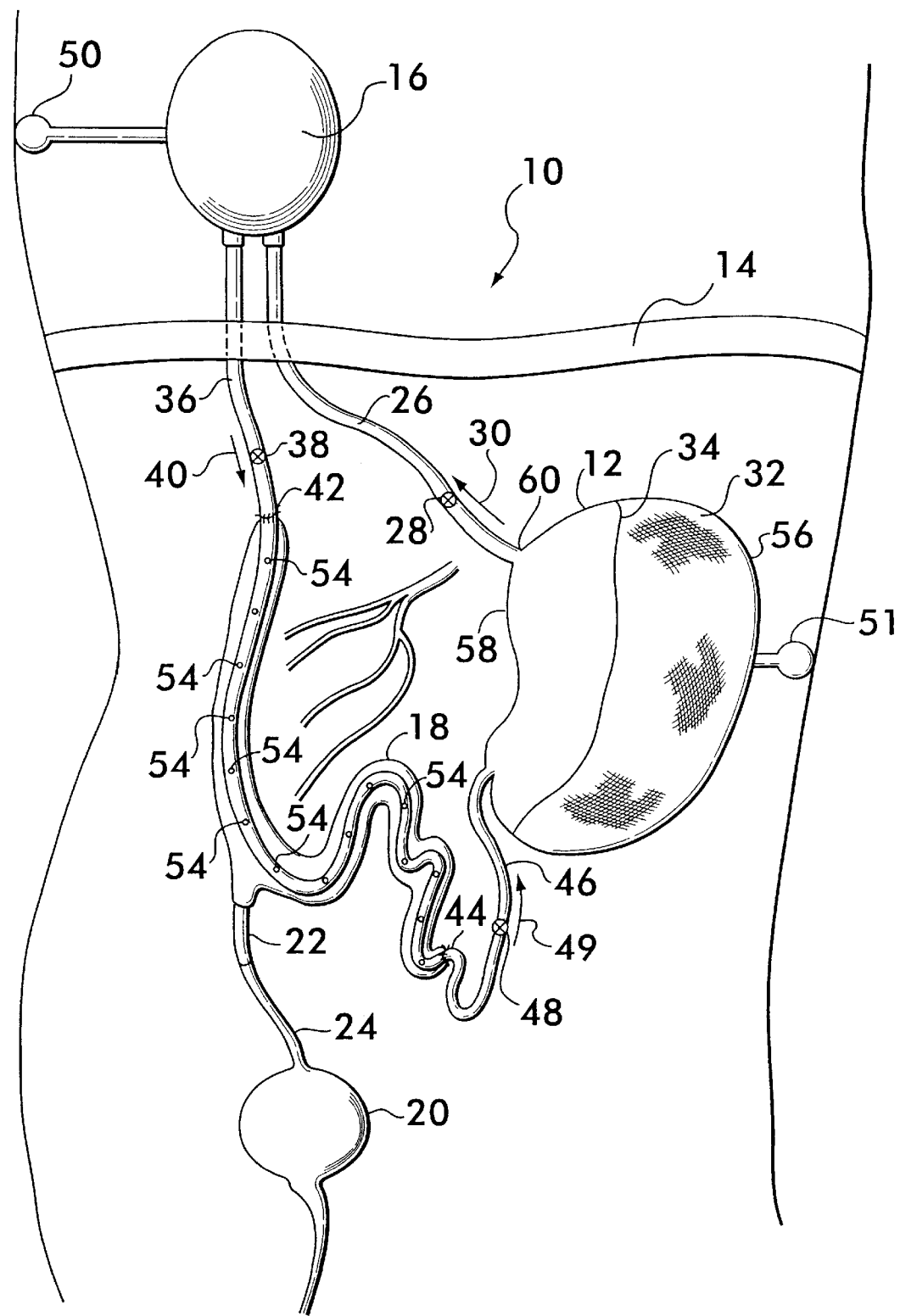
FIG. 1 is a front view of a continuous internal peritoneal dialysis prosthesis of a preferred embodiment of the present invention showing parts thereof in section and being located in a person's body.

Referring to FIG. 1, an exemplary continuous internal peritoneal dialysis prosthesis inserted within a patient's body is schematically illustrated at 10. The prosthesis 10 includes an abdominal sac 12 in the abdominal region of the patient below diaphragm 14, a thoracic pouch 16 in the thoracic region of a patient's body above the diaphragm 14, a section of a patient's bowel 18 located within the abdominal section of the patient, and the patient's urinary bladder 20 connected to a downstream end of the bowel 18 through the patient's cecum or appendix 22 and distal right ureter 24.

Still referring to FIG. 1, the abdominal sac 12 is connected to the thoracic pouch 16 through a conduit 26 including a one-way valve 28 therein. The one-way valve 28 permits fluid (e.g., unconcentrated urine) to flow only in the direction of arrow 30 from the abdominal sac 12 into the thoracic pouch 16.

The abdominal sac 12 includes a semi-permeable outer wall 56 and an impermeable outer wall 58 separated by a semi-permeable window 34. The region of the abdominal sac 12 defined by the semi-permeable outer wall 56 and the semi-permeable window 34 is a dialysis sac 32. The impermeable outer wall 58 includes a first port 60 for receiving a proximal end of the conduit 26. After the conduit 26 is in communication with the port 60, the wall of the abdominal sac 12 is stitched about the conduit 26 to retain the conduit within said port 60.

Still referring to FIG. 1, the prosthesis 10 includes a second conduit 36 that is connected to the thoracic pouch 16 and passes through the diaphragm 14 into and through a section of the patient's bowel 18. The second conduit 36 also includes a one-way valve 38 to permit the unconcentrated urine to flow from the thoracic pouch 16 through the section of the patient's bowel 18 only in the direction of the arrow 40.

As can be seen in FIG. 1, the patient's bowel 18 includes end sections sutured to the conduit 36 at both the entrance 42 to the bowel 18 and the exit 44 from the bowel 18. The distal end 46 of the second conduit 36 extends through a lower end of the bowel 18 and is connected to the abdominal sac 12 to recycle the flow of unconcentrated (or partially concentrated) urine back into the abdominal sac 12, as will be described in greater detail below. The distal end 46 is provided with a one-way valve 48 to permit the urine to flow only in the direction of arrow 49 from the patient's bowel 18 to the abdominal sac 12.

As noted earlier, the abdominal sac 12 is formed of an impermeable membrane at outer wall 58, and a semi-permeable membrane at outer wall 56 and window 34. The semi-permeable outer wall 56 and window 34 define the dialysis sac 32 of the abdominal sac 12. The semi-permeable membrane has pores or apertures (holes) that provide the membrane with a porosity which precludes dialysate within the dialysis sac 32 from escaping into the peritoneal region, but still permits unconcentrated urine within the peritoneal region to enter the dialysis sac 32 through osmotic pressure. The porosity of the semi-permeable window 34 also precludes dialysate within the dialysis sac 32 from filtering through the semi-permeable window 34 into the region of the abdominal sac 12 in communication with the conduits 26 and 36. Therefore, in this example of the preferred embodiment, the dialysate is contained within the dialysis sac 32. Because the abdominal sac 12 is required to function in an aqueous environment, it preferably is formed of a synthetic plastic material with some elastic qualities. However, the dialysis sac 32 should not be so elastic as to expand to an extent that permits the dialysate molecules or microstructures to exit from expanded pores of its walls.

In order to prevent the dialysis sac 32 from expanding to an extent that permits the dialysate to exit its walls, portions of the semi-permeable outer wall 56 and window 34 may alternatively be formed of an impermeable or substantially impermeable membrane that is more elastic than the semi-permeable membrane and does not permit the dialysate to exit, even when the impermeable or substantially impermeable membrane is expanded beyond its elastic limit. Therefore, before the semi-permeable membrane expands under pressure to an extent that could permit dialysate to exit, the impermeable or substantially impermeable membrane stretches to contain the dialysate while inhibiting the dialysate from exiting therefrom. Also, impermeable wall 58 could be made elastic and semi-permeable walls 56 and 34 inelastic.

In an exemplary environment of this invention, the dialysate exerts chemical potential to draw in unconcentrated urine (e.g., fluid wastes, electrolytes, etc.) via the adjacent peritoneum and mesenteric parieties. The dialysate can be a large inert molecule or microstructure, e.g., microspheres, such as a 50 micron polyelectrolyte or L-racemate of any giant inert molecule which cannot exit the sac. It should be understood that, in accordance with the broadest aspects of this invention, the specific dialysate employed does not constitute a limitation on the present invention. However, the particle size of the dialysate must be such that the dialysate does not escape through the semi-permeable membrane walls of the dialysis sac 32 during operation of the prosthesis 10.

Ideally, the pores or apertures in the semi-permeable membrane should be about 10 microns non-expanded to about 20 microns expanded, while the dialysis molecule should have a nominal size in the range of 50 to 100 microns. Of course, these numerical values are disclosed for purposes of illustration only, and are not intended to limit the scope of the present invention.

The semi-permeable membrane can be made of any suitable synthetic plastic material, such as a Gortex-like cloth, and the dialysate can be made from a wide variety of molecules or microstructures well-known to those skilled in the art. The thoracic pouch 16, first conduit 26, second conduit 36 and impermeable outer wall 58 of the abdominal sac 12 are preferably made from silicon plastic, which is inert and does not cause peritoneal irritation.

In the preferred form of this invention, the dialysis sac 32 is positioned between the peritoneum and mesenteric parieties in the left lower quadrant of the abdomen to extract fluids (unconcentrated urine) via osmotic diffusion and ultra filtration by the same physiological principles that control regular peritoneal dialysis. The dialysis sac 32 swells with unconcentrated urine which then traverses the window 34 shared with the abdominal sac 12. As shown in FIG. 1, the dialysate does not leave the dialysis sac 32 and therefore cannot be absorbed by the lymphatic system or irritate the peritoneum. The unconcentrated urine entering the dialysis sac 32 through the semi-permeable membrane and exiting through the window 34 will then be directed through the first conduit 26 and the one-way valve 28, through the diaphragm 14 and into the thoracic pouch 16 by the internal body pumping mechanism based on relative pressure changes in the abdomen and thorax during the breathing cycle, as described later in this application. It should be understood that neither the conduit 26 nor the thoracic pouch 16 have any permeability, i.e., they are impermeable so as to preclude the escape of any unconcentrated urine therefrom.

As is shown in FIG. 1, the abdominal sac 12 and the thoracic pouch 16 communicate with subcutaneous access reservoirs 50 and 51, respectively, each of which include an access section closely adjacent the patient's skin. The subcutaneous access reservoirs (SARs) 50 and 51, permit the monitoring and testing of the urine in order to determine the effectiveness of the prosthesis. The subcutaneous access reservoirs 50 and 51 provide adjustments of urine flow and urine constituents by adding or subtracting dialysate to fit each patient's needs. The dialysate can be added or withdrawn from the subcutaneous access reservoirs 50 and 51 using a syringe or tube inserted through the patient's skin into the reservoirs.

The unconcentrated urine within the thoracic pouch 16 then passes through the second conduit 36 and one-way valve 38 therein to a section of the patient's bowel 18. Movement of the unconcentrated urine from the thoracic pouch 16 through the second conduit 36 takes place by an internal pumping mechanism to be described in greater detail hereinafter. Suffice it to state at this time that the second conduit 36 traverses a relatively long segment of bowel that has been isolated from the rest of the bowel. The segment that preferably is selected includes the right colon and ileum, and is capable of 90% water reabsorption in the bowel, which translates to 10 to 20 liters of water per day.

The movement of the unconcentrated urine through the bowel 18 is a unique feature of the present invention. The second conduit 36, which directs the unconcentrated urine into the segment of the patient's bowel 18 includes a series of relatively large holes (or apertures) 54, e.g., one-half cm, so as to allow the unconcentrated urine within the conduit 36 to move into the bowel 18, wherein the bowel 18 functions to reabsorb water, electrolytes and small molecules, resulting in the formation of concentrated urine. The bowel will not absorb large molecules, standard excretory wastes and other poisons, or even standard proteins. It should be noted that the jejunum is anastomosed to transverse colon to restore the integrity of the GI tract, and therefore, though the section patient's bowel 18 is isolated, its blood supply remains intact so as to permit it to function in this invention.

Some of the concentrated urine will traverse the appendix 22, which has a one-way peristalsis to the bladder 20, which appropriately excretes the concentrated urine based on the bladder's normal function. The remaining urine is returned through the distal end 46 of the conduit 36 to the abdominal sac 12 for recirculation and recleansing. This distal end 46 of the conduit 36 is impermeable to preclude the escape of any urine therefrom.

It is important to note that in this exemplary prosthesis of this preferred embodiment, there is no free dialysate in the peritoneal cavity; said dialysate being retained in the dialysate sac 32. It is only in such a system that it is both safe and advantageous for there to be emphatic reabsorption.

In fact, it should be noted that in prior art peritoneal dialysis the reabsorption of dialysate and unconcentrated urine creates a major problem for two reasons. First, it interferes with the vary process of discarding this excessive fluid. Second, any system in which dialysate is reabsorbed causes two other problems, the first of which is that it interferes with the very difference in osmotic pressure needed for the whole process of diffusion and ultra filtration, and secondarily, even if the dialysate molecule is inert versus the sugar, salt or albumin used in standard dialysis, each of which causes its own special problems when reabsorbed by the lymphatic system, it creates a tremendous problem with oncotic pressure.

Therefore, it should be emphasized that the continuous internal peritoneal dialysis prosthesis and method of this preferred embodiment is highly advantageous because the dialysate itself is separate at all times from the peritoneal space and from lymphatic absorption. The fact that some partially concentrated urine is recycled in the present invention is also advantageous. In particular, this recycling of partially concentrated urine allows for further cleansing of nitrogenous wastes from the urine and is precisely the same thing that happens during urine formation in a kidney that is functioning normally.

It also should be noted that, in a manner identical to the functioning of a normal kidney, the lower the serum osmolality (the more liquids a patient consumes) the better the peritoneal system of this invention works. In particular, the greater the differential between the osmotic pressure in the dialysis sac 32 employed in this invention and the blood (serum osmolality) the more urine is made. Therefore, the patient employing the prosthesis of this invention is able to drink as much as he or she wants, unlike other dialysis patients, because his/her increased intake of water simply increases the performance of the prosthesis of this invention. This is a significant benefit of the present invention.

As noted earlier, when the unconcentrated urine is turned into concentrated urine within the section of the patient's bowel 18, most of the concentrated urine will exit to the distal right ureter 24, which can be attached to the cecum or appendix 22 when appropriate, and this concentrated urine, of course, would then go into the urinary bladder 20 to be expelled intermittently, just as in a normally functioning human patient.

It should be noted that the process is continuous and prevents sudden changes in volume and concentration of the blood's constituents. The continuous operation of the prosthesis of this invention relies upon the internal body pumping action of the disclosed system. This internal body pumping action is a variation of the internal body pump and systems disclosed in Applicant's U.S. Pat. No. 5,813,410. The entire subject matter of this latter patent is hereby incorporated by reference herein.

However, by way of explanation, the fluid is circulated through the prosthesis 10 of this invention by means of a body-operated pump, e.g., the abdominal sac 12 and thoracic pouch 16 serve as pumps operated by a patient's breathing pattern to cause the fluid to flow through the prosthesis. In particular, fluid flow within the prosthesis 10 is created by taking advantage of the normal function of a person's diaphragm 14 and the normal internal pressure relationships that exist between the thoracic cavity and the abdominal cavity of the person's body while a person is breathing. Specifically, during inspiration (inhaling) the diaphragm, which separates the thoracic and abdominal cavities, is forced to descend; thereby leading to an increase in the intra thoracic volume and a corresponding decrease in the intra thoracic pressure. Conversely, the volume of the abdominal cavity decreases and the pressure in that cavity increases. This action forces fluid from the abdominal sac 12 located in the abdominal cavity through conduit 26 and into the thoracic pouch 16 in the thoracic cavity. The flow from the abdominal sac 12 to the thoracic pouch 16 is limited to flowing through the conduit 26 only in the direction of arrow 30, due to the arrangement of the one-way valve 28 in that conduit 26.

Upon expiration (exhaling) the operation of the diaphragm is reversed. That is, the diaphragm is forced to rise; thereby leading to a decrease in the intra thoracic volume and the corresponding increase in the intra thoracic pressure. Conversely, during expiration, the volume of the abdominal cavity increases and the pressure in that cavity decreases. This action forces fluid from the thoracic pouch 16, located in the thoracic cavity, preferably in the costo phrenic sulcus thereof, to flow through the conduit 36, and into the section of the patient's bowel 18 for delivery into the urinary bladder 20 or back into the abdominal sac 12. Fluid flow from the thoracic pouch 16 through the bowel section 18 is limited to flowing only in the direction of arrow 40, due to the inclusion of the one-way valve 38 in the second conduit 36. Likewise, fluid flow from the bowel section 18 to the abdominal sac 12 is limited to flowing only in the direction of arrow 49, due to the inclusion of the one-way valve 48.

As should be appreciated from the foregoing, in operation the unconcentrated urine which is directed into the dialysis sac 32 is continuously moved through the prosthesis 10 by the breathing cycle of a patient, as described. The unconcentrated urine directed through the second conduit 36 into the bowel section 18 is then processed by the bowel section to concentrate the urine for ultimate removal through the urinary bladder 20.

If necessary, or desired, the pumping action provided by the breathing cycle of the patient can be augmented, or even supplanted, by another device, e.g., a mechanical or electrical pump implanted in the person's body in fluid communication with the loop of circulating fluid.

Figure 2:
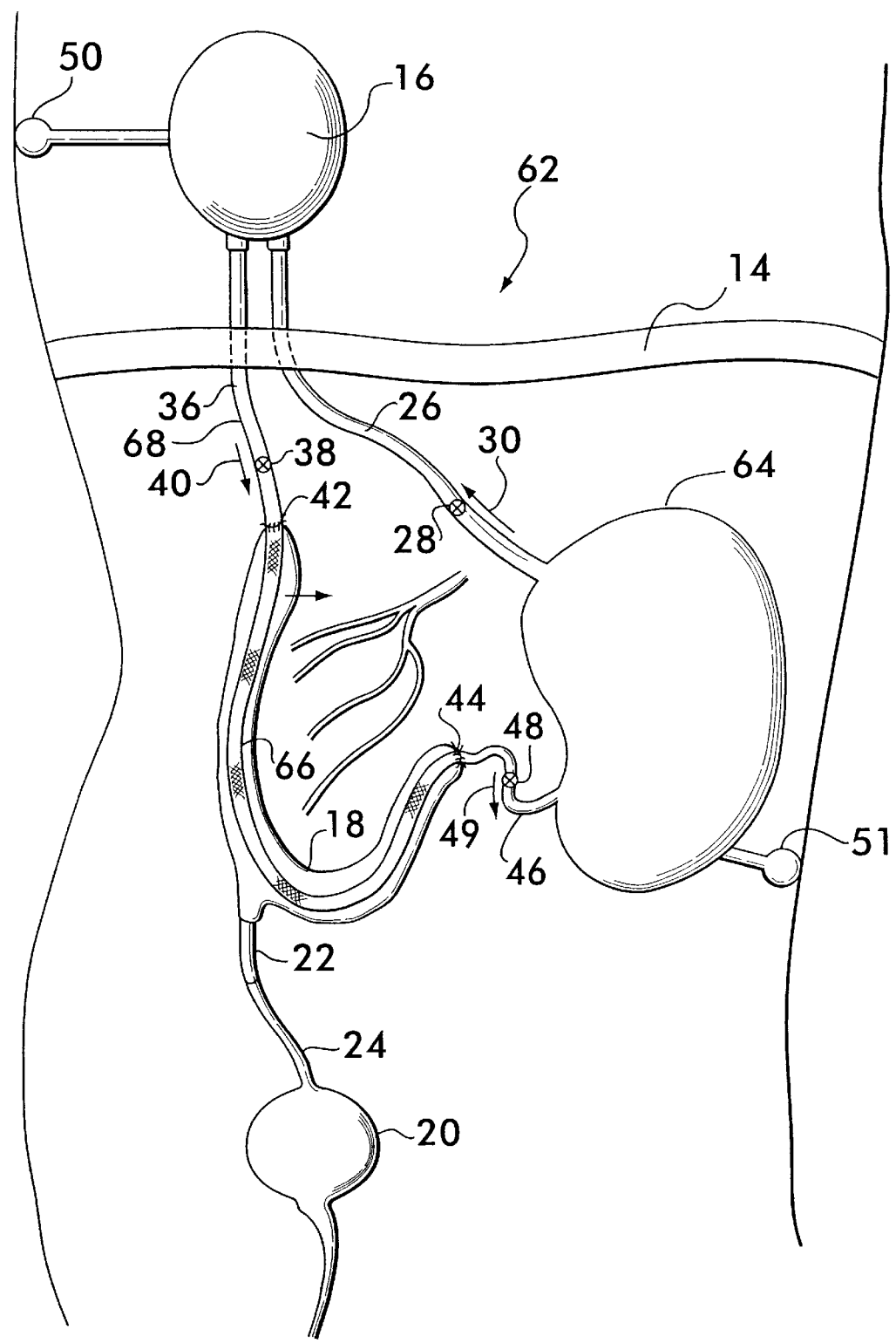
FIG. 2 is a front view of a continuous internal peritoneal dialysis prosthesis of another preferred embodiment of the present invention showing parts thereof in section and being located in a person's body.

Referring to FIG. 2, there is shown at 62, an exemplary continuous internal peritoneal dialysis prosthesis inserted within a patient's body in accordance with a second preferred embodiment of this invention, which is similar to the prosthesis 10 discussed above and illustrated in FIG. 1. As shown in FIG. 2, the prosthesis 62 includes an abdominal sac 64 in the abdominal region of the patient below diaphragm 14, a thoracic pouch 16 in the thoracic region of the patient's body above the diaphragm 14, a section of the patient's bowel 18 located within the abdominal section of the patient, and the patient's urinary bladder 20 connected to a downstream end of the bowel 18 through the patient's cecum or appendix 22 and distal right ureter 24. The abdominal sac 64 is connected to the thoracic pouch 16 through a conduit 26, including a one-way valve 28 therein. The one-way valve 28 permits fluid to flow only in the direction of arrow 30 from the abdominal sac 64 into the thoracic pouch 16.

The prosthesis 62 includes a second conduit 36 having a proximal end 68 and a distal end 46. This second conduit 36 is connected to the thoracic pouch 16 through its proximal end 68 and passes through the diaphragm 14 into and through a section of the patient's bowel 18. The second conduit includes a one-way valve 38 at its proximal end 68 to permit the unconcentrated urine to flow from the thoracic pouch 16 through the section of the patient's bowel 18 only in the direction of arrow 40. The distal end 46 of the second conduit 36 extends through a lower end of the bowel 18 and is connected to the abdominal sac 64 to recycle the flow of unconcentrated (or partially concentrated) urine back into the abdominal sac 64. The distal end 46 is provided with a one-way valve 48 to permit the urine to flow only in the direction of arrow 49 from the patient's bowel 18 to the abdominal sac 64. The patient's bowel 18 is sutured to the conduit 36 at both the entrance 42 to the bowel 18 and the exit 44 from the bowel 18.

As noted above, the prosthesis 62 shown in FIG. 2 is constructed similar to the prosthesis 10 shown in FIG. 1. However, in this embodiment, the dialysate is not contained only within a dialysis sac. In fact, the abdominal sac 64 does not include or share a window with a dialysis sac. In FIG. 2, the abdominal sac 64, thoracic pouch 16 and conduits 26 and 36 provide a closed system for the dialysate, allowing the dialysate to cycle within the prosthesis 62, but preventing the dialysate from leaving the prosthesis 62.

The abdominal sac 64 is generally formed of a semi-permeable membrane having a porosity which precludes the dialysate within the abdominal sac 64 from escaping into the peritoneal region, but still permits unconcentrated urine within the peritoneal region to enter the abdominal sac 64 through osmotic pressure. Because the abdominal sac 64 is required to function in an aqueous environment, it preferably is formed of a synthetic plastic material with some elastic qualities (e.g., Gortex-like cloth). However, the abdominal sac 64 should not be so elastic as to expand to an extent that permits the dialysate molecules or microstructures to exit from expanded pores of its walls.

The abdominal sac 64 may be similar to the abdominal sac 12 shown in FIG. 1, but without the wall 34. As with the abdominal sac 12 of FIG. 1, portions of the wall of the abdominal sac 64 may alternatively be formed of an impermeable or substantially impermeable membrane that is more elastic than the semi-permeable membrane and does not permit the dialysate to exit, even when the impermeable or substantially impermeable membrane is expanded beyond its elastic limit. Therefore, before the semi-permeable membrane expands under pressure to an extent that could permit dialysate to exit, the impermeable or substantially impermeable membrane stretches to contain the dialysate while inhibiting the dialysate from exiting therefrom.

As noted earlier, the section of the patient's bowel 18 is sutured to the conduit 36 at both the entrance 42 to the bowel 18 and the exit 44 from the bowel 18, thereby enclosing a central region 66 of the conduit 36. This central section 66 includes a semi-permeable wall so as to allow the unconcentrated urine within the central region of the second conduit 36 to move into the bowel 18, wherein the bowel functions to reabsorb water, electrolytes and small molecules, resulting in concentrated urine. However, the semi-permeable wall prevents the dialysate from moving into the bowel, thus keeping the dialysate within the prosthesis 62. It should be understood that neither the conduit 26, the thoracic pouch 16, nor the proximal end 68 of the conduit 36 have any permeability, i.e., they are impermeable so as to preclude the escape of any unconcentrated urine or dialysate therefrom.

As is shown in FIG. 2, the unconcentrated urine entering the abdominal sac 64 through the semi-permeable membrane, and the dialysate are directed through the first conduit 26 and the one-way valve 28, through the diaphragm 14 and into the thoracic pouch 16 by the internal body pumping mechanism described above. The unconcentrated urine and dialysate within the thoracic pouch 16 then pass through the second conduit 36 and one-way valve 38 therein to a section of the patient's bowel 18. Movement of the unconcentrated urine and dialysate from the thoracic pouch 16 through the second conduit 36 takes place by the internal body pumping mechanism described above. As mentioned above, the central region 66 of the second conduit 36, which directs the unconcentrated urine and dialysate into the segment of the patient's bowel 18 is formed of a semi-permeable membrane so as to allow the unconcentrated urine within the conduit 36 to move into the bowel, wherein the bowel functions to reabsorb water, electrolytes and small molecules, resulting in concentrated urine. However, the semi-permeable membrane prevents the dialysate from leaving the second conduit 36.

In a manner similar to the prosthesis shown in FIG. 1, some of the concentrated urine in FIG. 2 will traverse the appendix 22, which has a one-way peristalsis to the bladder 20, which appropriately excretes the concentrated urine based on the bladder's normal function. The remaining urine (unconcentrated and partially concentrated) is returned with the dialysate through the distal end 46 of the conduit 36 to the abdominal sac 64 for circulating and recleansing. Preferably, the distal end 46 of the conduit 36 is impermeable to preclude the escape of any urine and dialysate therefrom.

Typically in chronic peritoneal dialysis, the dialysate is introduced directly into the peritoneal space via a catheter and removed after it has drawn in urine. Introducing the dialysate into the peritoneal space presents problem with the chronic peritoneal dialysis procedure. Peritoneal irritation and chronic thickening caused by the dialysis leads to poor diffusion and ultra filtration. In addition, the dialysate in the peritoneal space can cause problems in the bloodstream (e.g., hypertonic sugar, hypertonic salt, increases in nitrogenous wastes, and problems in the bloodstream including bleeding and clotting disorders, poisoning various enzyme systems, antigen-antibody reactions, D-C, etc.).

The embodiments of the invention discussed above and illustrated in FIGS. 1 and 2 do not suffer from these problems because the dialysate cannot filter through the semi-permeable membrane. However, the embodiments of the invention discussed below allow for direct contact of the dialysate with the peritoneum. The continuous internal peritoneal dialysis prosthesis discussed below are of greater benefit when using a dialysate that cannot be absorbed by the lymphatic system or where there is minimal absorption of the dialysate without toxicity.

Figure 3:
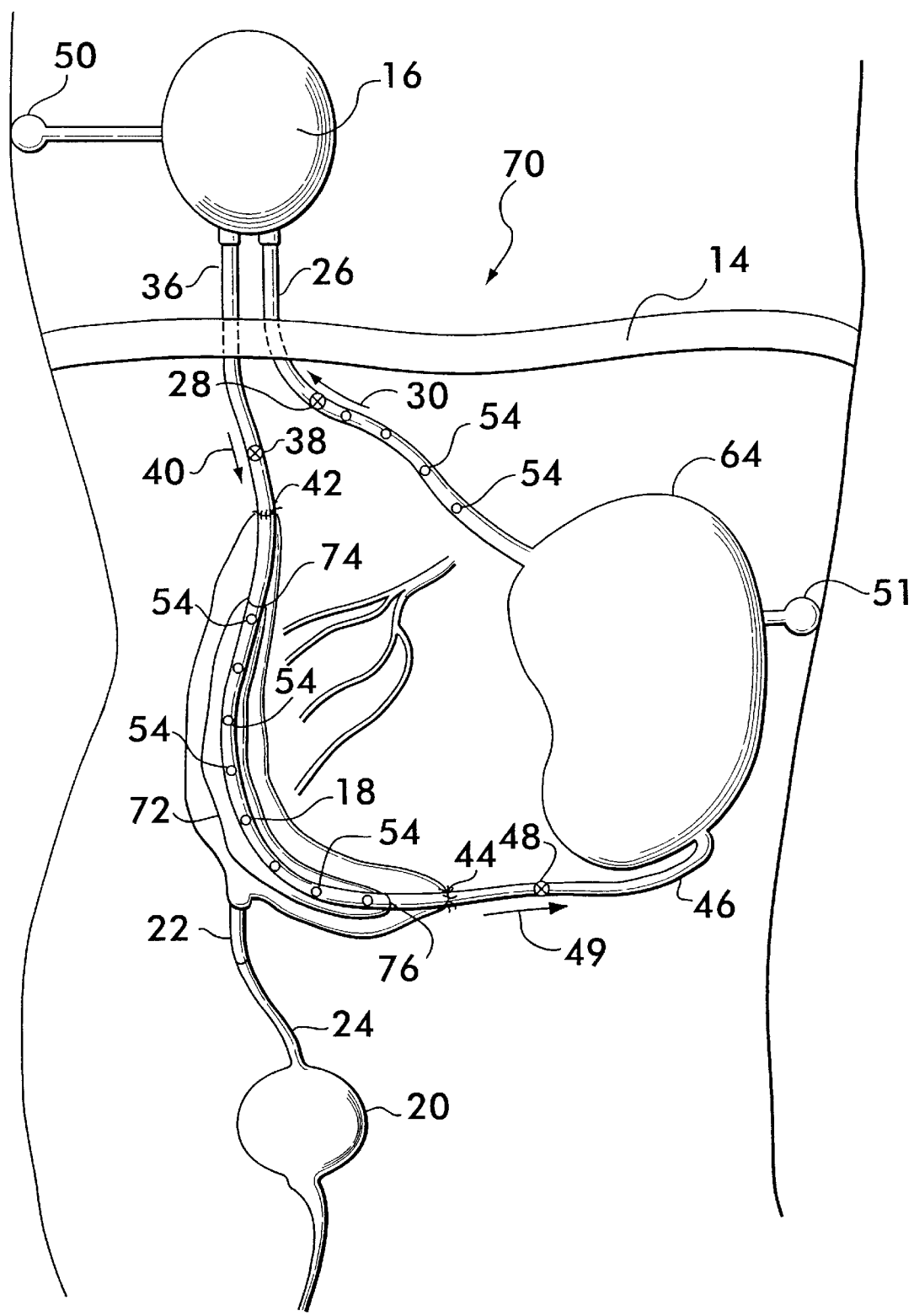
FIG. 3 is a front view of a continuous internal peritoneal dialysis prosthesis of a third embodiment of the present invention showing parts thereof in section and being located in a person's body.

Referring to FIG. 3, an exemplary continuous internal peritoneal dialysis prosthesis inserted within a patient's body is schematically illustrated at 70. The prosthesis 70 includes an abdominal sac 64 in the abdominal region of the patient below the diaphragm 14, a thoracic pouch 16 in the thoracic region of the patient's body above the diaphragm 14, a section of a patient's bowel 18 located within the abdominal region, conduits 26 and 36 connected between the abdominal sac 64 and the thoracic pouch 16, and a semi-permeable membrane 72 enclosed within the bowel 18. The abdominal sac 64, thoracic pouch 16, bowel 18, and conduits 26 and 36 are similar to the like elements shown in FIG. 2. However, the conduits 26 and 36 include a series of relatively large holes 54 (e.g., one-half centimeter) that allow urine and dialysate to permeate therethrough, as will be described later.

The abdominal sac 64 may be similar to the abdominal sac 12 shown in FIG. 1, but without the wall 34. As with the abdominal sac 12 of FIG. 1, portions of the abdominal sac 64 may alternatively be formed of an impermeable or substantially impermeable membrane that is more elastic than the semi-permeable membrane and does not permit the dialysate to exit, even when the impermeable or substantially impermeable membrane is expanded beyond its elastic limit. Therefore, before the semi-permeable membrane expands under pressure to an extent that could permit dialysate to exit, the impermeable or substantially impermeable membrane stretches to contain the dialysate while inhibiting the dialysate from exiting therefrom.

As can be seen in FIG. 3, the section of the patient's bowel 18 is sutured to the conduit 36 at both the entrance 42 to the bowel 18 and the exit 44 from the bowel 18. The semi-permeable membrane 72 extends about the second conduit 36 within the bowel 18 and is attached to the second conduit 36 at both the entrance 74 to the membrane 72 and the exit 76 from the membrane 72. The semi-permeable membrane 72 is preferably a synthetic plastic material with some elastic qualities having a porosity which precludes dialysate from filtering through the semi-permeable membrane, but permits unconcentrated urine to filter through the material.

In this embodiment, both the dialysate and unconcentrated urine are present in the peritoneal region. The abdominal sac 64 receives unconcentrated urine and dialysate via the relatively large holes 54 of the first conduit 26. In addition, the abdominal sac 64 receives unconcentrated urine through sections of the wall of the abdominal sac 64 that are made of semi-permeable membrane.

The unconcentrated urine and dialysate entering the abdominal sac 64 is directed through the first conduit 26 and the one-way valve 28, through the diaphragm 14 and into the thoracic pouch 16 by the internal body pumping mechanism described above. Unconcentrated urine and dialysate also flow from the peritoneum through the relatively large holes 54 into the first conduit 26, and is directed toward the thoracic pouch 16. The unconcentrated urine and dialysate within the thoracic pouch 16 then pass through the second conduit 36 and the one-way valve 38 therein to a section of the patient's bowel 18. Movement of the unconcentrated urine and dialysate from the thoracic pouch 16 through the second conduit 36 takes place by the internal pumping mechanism described above, which may be assisted or supplemented with a pump. As noted above, the second conduit 36 which directs the unconcentrated urine and dialysate into the segment of the patient's bowel 18 includes a series of relatively large holes 54 so as to allow the unconcentrated urine and dialysate within the second conduit 36 to flow out of the conduit 36. The semi-permeable membrane 72 that is within the bowel 18 has a porosity which precludes the dialysate that filtered through the holes 54 of the second conduit 36 from escaping into the bowel 18, but still permits the unconcentrated urine to permeate into the bowel 18, wherein the bowel 18 functions to reabsorb water, electrolytes and small molecules resulting in concentrated urine.

As noted earlier, when the unconcentrated urine is turned into concentrated urine within the section of the patient's bowel 18, most of the concentrated urine will exit to the distal right ureter 24, which can be attached to the cecum or appendix 22 when appropriate. The concentrated urine will then flow into the urinary bladder 20 to be expelled intermittently, just as in a normally functioning human patient. The dialysate and returning urine is returned through the distal end 46 of the conduit 36 to the abdominal sac 64 for recirculation and recycling. This distal end 46 of the conduit 36, and the sections of the conduits 26 and 36 above the diaphragm 14 are impermeable to preclude the escape of any urine or dialysate therefrom.

Figure 4:
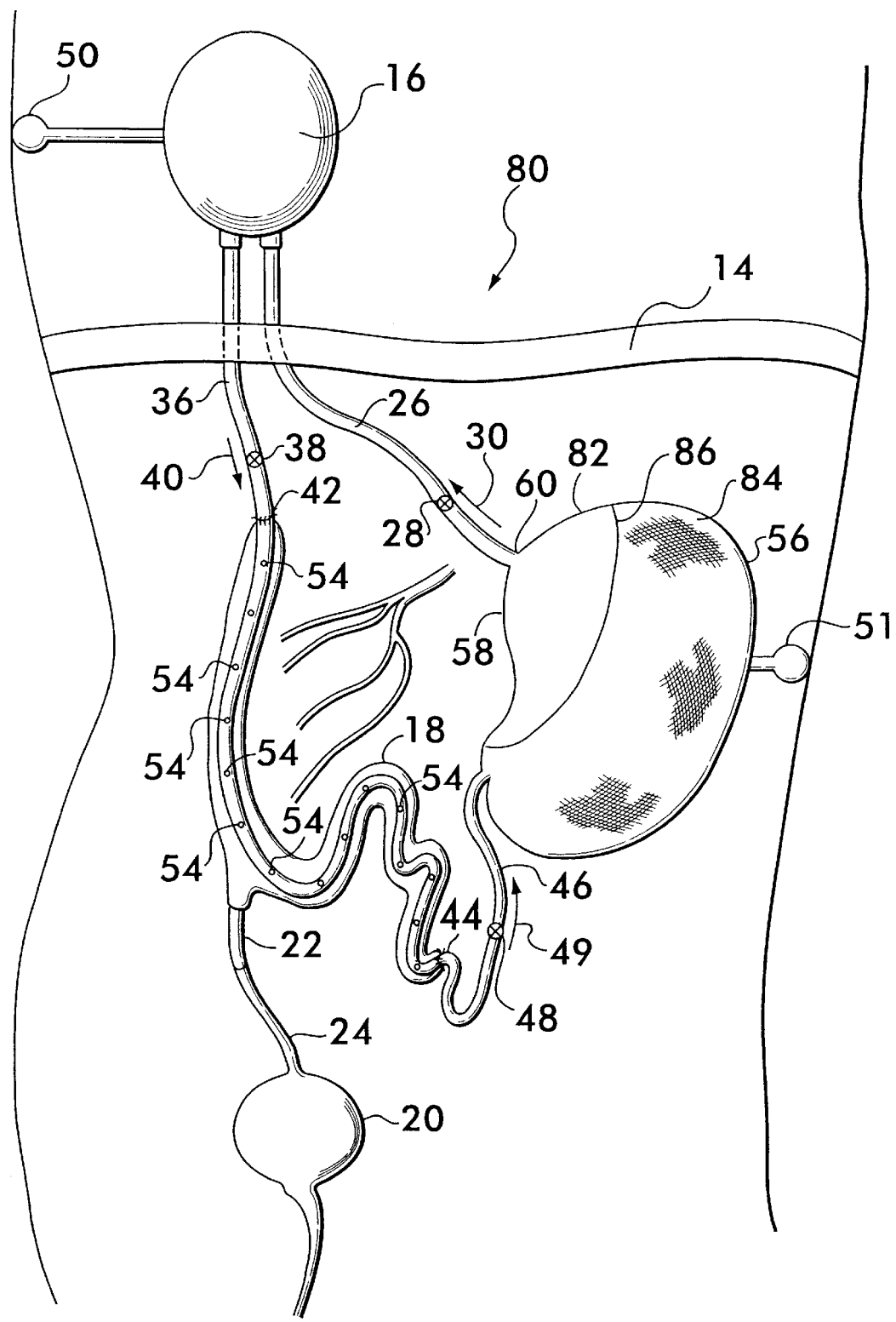
FIG. 4 is a front view of a continuous internal peritoneal dialysis prosthesis of a fourth embodiment of the present invention showing parts thereof in section and being located in a person's body.

FIG. 4 is still another embodiment of the invention wherein dialysate is in direct contact with the peritoneum. Referring to FIG. 4, an exemplary continuous internal peritoneal dialysis prosthesis inserted within a patient's body is schematically illustrated at 80 and is similar to the prosthesis is shown in FIG. 1. The prosthesis 80 includes an abdominal sac 82 in the abdominal region of the patient below diaphragm 14, a thoracic pouch 16 in the thoracic region of the patient's body above the diaphragm 14, a section of the patient's bowel 18 located within the abdominal section of the patient and a urinary bladder 20 connected to a downstream end of the bowel 18 through the patient's cecum or appendix 22 and distal right ureter 24.

The abdominal sac 82 includes a semi-permeable outer wall 56 and an impermeable outer wall 58 separated by a semi-permeable window 86. The region of the abdominal sac 82 defined by the semi-permeable outer wall 56 and the semi-permeable window 86 is a dialysis sac 84. The semi-permeable outer wall 84 and window 86 are formed of a semi-permeable membrane as discussed in detail above. The abdominal sac 82, dialysis sac 84, thoracic pouch 16, first conduit 26, bowel 18 and second conduit 36 shown in FIG. 4 are substantially similar to the abdominal sac 12, dialysis sac 32, thoracic pouch 16, first conduit 26, bowel 18 and second conduit 36 shown in FIG. 1. However, instead of the distal end 46 of the second conduit 36 being formed of an impermeable material and connected to the abdominal pouch 12 (FIG. 1), the distal end 46 of FIG. 4 includes a series of relatively large holes 54 (e.g., one-half centimeter) and is connected to the semi-permeable outer wall 56 of the dialysis sac 84.

The distal end 46 includes the holes 54 so as to allow unconcentrated urine and dialysate in the peritoneum to move into the conduit 36 and then into the dialysis sac 84. The dialysate is contained within the distal end 46 of the conduit 36 and the dialysis sac 84 and does not flow through the remainder of the prosthesis 80. The one-way valve 48 permits the unconcentrated and partially concentrated urine exiting from the second conduit 36 in the bowel 18 to travel towards the dialysis sac 84, but does not allow fluid, including the dialysate, to enter the second conduit 36 in the bowel 18 from the distal end 46.

In FIG. 4, unconcentrated urine flows from the abdominal sac 82 through the first conduit 26 and one-way valve 28 through the diaphragm 14 to the thoracic pouch 16. The unconcentrated urine within the thoracic pouch 16 then passes through the diaphragm 14 and one-way valve 38 in the second conduit to the patient's bowel 18. Movement of the urine through the prosthesis 10 takes place by the internal pumping mechanism described in detail above.

As noted earlier during the discussion of FIG. 1, the second conduit 36 of FIG. 4, which directs the unconcentrated urine into the segment of the patient's bowel 18, includes a series of relatively large holes 54. The holes 54 allow the unconcentrated urine within the conduit 36 to move into the bowel 18, wherein the bowel 18 functions to reabsorb water, electrolytes and small molecules resulting in concentrated urine. Some of the concentrated urine will traverse the appendix 22 which has a one-way peristalsis to the bladder 20, which appropriately excretes the concentrated urine based on the bladder's normal function. The remaining urine is returned through the distal end 46 of the conduit 36 (where it is mixed with unconcentrated urine and dialysate from the peritoneum) to the dialysis sac 84 for recirculation and recleansing.

In order to prevent the dialysis sac 84 from expanding to an extent that permits the dialysate to exit the walls, portions of the semi-permeable outer wall 56 and the semi-permeable window 86 may alternatively be formed of an impermeable or substantially impermeable membrane that is more elastic than the semi-permeable membrane and does not permit the dialysate to exit, even when the impermeable or substantially impermeable membrane is expanded beyond its elastic limit. Therefore, before the semi-permeable membrane expands under pressure to an extent that could permit dialysate to exit, the impermeable or substantially impermeable membrane stretches to contain the dialysate while inhibiting the dialysate from exiting therefrom. Also, the impermeable wall 58 could be made elastic and the semi-permeable wall 56 and window 86 made inelastic.

Although the conduits 26 and 36 are illustrated in the exemplary embodiments shown in FIGS. 1-4 as being separate conduits spaced apart from each other and extending through separate passages in the diaphragm 14, it should be understood that, in a preferred construction, the conduits 26 and 36 are interconnected together and pass through only a single aperture in the diaphragm 14. The spaced apart arrangement of the conduits 26 and 36 is shown in the drawings for purposes of clarity.

The operation of all of the embodied prostheses shown in FIGS. 1-4 is preferably continuous and relies upon the internal body pumping action of the disclosed systems. This internal body pumping action is described in relation to FIG. 1 and is substantially similar in operation for the other exemplary embodiments shown in FIGS. 2-4 as a skilled artesian would readily understand. The described internal body pumping action is a variation of the internal body pump and systems disclosed in Applicant's U.S. Pat. No. 5,813,410, the entire subject matter of which is incorporated by reference herein. In addition, for all of the exemplary embodiments, the pumping action provided by the breathing cycle of the patient can be augmented, or even supplanted, by another device (e.g., a mechanical or electrical pump implanted in the person's body in fluid communication with the loop of circulating fluid).

Figure 5:
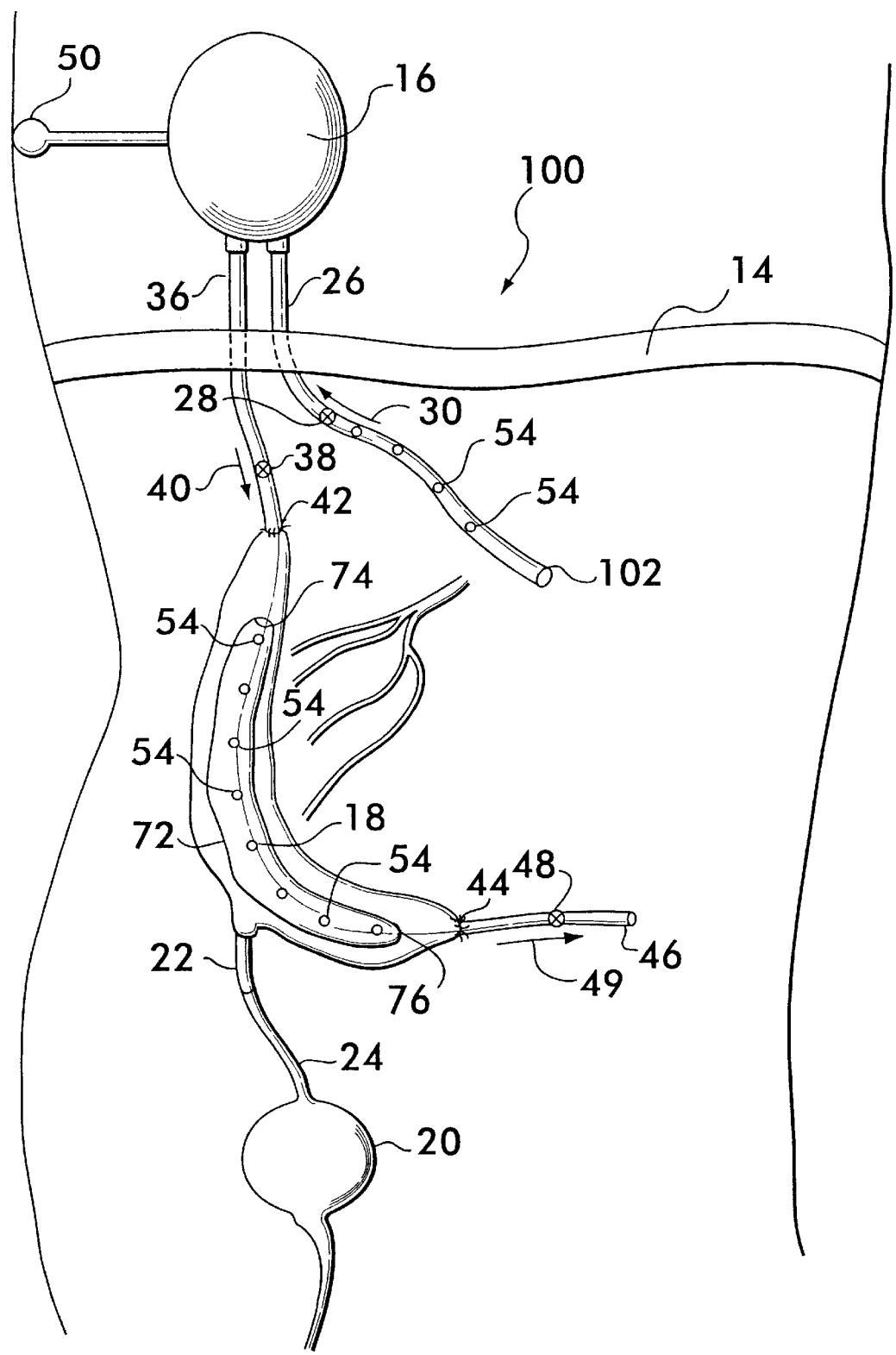
FIG. 5 is a front view of a continuous internal peritoneal dialysis prosthesis of a fifth embodiment of the present invention showing parts thereof in section and being located in a person's body.

Referring to FIG. 5, a further and preferred exemplary continuous peritoneal dialysis prosthesis inserted within a person's body is schematically illustrated at 100. The prosthesis 100 includes a thoracic pouch 16 in the thoracic region of the patient's body above the diaphragm 14, a section of the patient's bowel 18 located within the abdominal region, conduits 26 and 36 communicating between the thoracic pouch 16 and the abdominal region, and a semi-permeable membrane 72 enclosed within the bowel 18. The thoracic pouch 16, bowel 18, and conduits 26 and 36 are similar to the like elements shown in FIG. 3. However, this embodiment is different than the embodiment shown in FIG. 3 because this embodiment omits the abdominal sac disclosed in FIG. 3.

As can be seen in FIG. 5, the section of the patient's bowel 18 is sutured to the conduit 36 at both the entrance 42 to the bowel 18 and the exit 44 from the bowel 18. The semi-permeable membrane 72 extends about the second conduit 36 within the bowel 18 and is attached to the second conduit 36 at both the entrance 74 to the membrane 72 and the exit 76 from the membrane 72. The semi-permeable membrane 72 is preferably a synthetic plastic material with some elastic qualities having a porosity which precludes dialysate from filtering through the semi-permeable membrane, but permits unconcentrated urine to filter through the material. The conduits 26 and 36 include a series of relatively large holes 54 (e.g., about one-half centimeter) that allow urine and dialysate to permeate therethrough as will described later.

In this embodiment, both the dialysate and unconcentrated urine are present in the peritoneal region. The first conduit receives unconcentrated urine and dialysate via the relatively large holes 54 and distal opening 102. The unconcentrated urine and dialysate is directed through the first conduit 26 and the one-way valve 28, through the diaphragm 14 and into the thoracic pouch 16 by the internal body pumping mechanism described above. The unconcentrated urine and dialysate within the thoracic pouch 16 then pass through the second conduit 36 and the one-way valve 38 therein to a section of the patient's bowel 18. Movement of the unconcentrated urine and dialysate from the thoracic pouch 16 through the second conduit 36 takes place by the internal pumping mechanism described above, which may be assisted or supplemented with a pump. In particular, the thoracic pump 16 serves as a pump influenced by a patient's breathing pattern to cause the unconcentrated urine and dialysate to flow through the prosthesis 100.

The prosthesis 100 omits the abdominal sac disclosed in the other embodiments of this invention and generally employs the peritoneal region as the "sac" region for retaining dialysate and unconcentrated urine. Accordingly, like the prosthesis shown above in FIGS. 3 and 4, the prosthesis 100 is of greatest benefit when using a dialysate that cannot be absorbed by the lymphatic system or where there is minimal absorption of the dialysate without toxicity (e.g., absorbable albumin). Because the dialysate is not contained within a separate abdominal sac, it is preferred that dialysate is added to the prosthesis (e.g., about 1 liter every few days) to ensure that a sufficient amount of dialysate is retained within the peritoneal region.

It should be apparent that the unconcentrated urine and dialysate does not flow through the prosthesis 100 as efficiently as the fluids flow through the embodiments discussed above that include both an abdominal sac and a thoracic pouch. Without an abdominal sac, the prosthesis does not form a closed loop and the thoracic pouch is relied upon to cause the fluid to flow through the prosthesis without the aid of an abdominal sac, as described above. Accordingly, this embodiment may be better suited for a patient that has only partial kidney failure.

As noted above, the second conduit 36 which directs the unconcentrated urine and dialysate into a segment of the patient's bowel 18 includes a series of relatively large holes 54 so as to allow the unconcentrated urine and dialysate within the second conduit 36 to flow out of the conduit. The semi-permeable membrane 72 that is within the bowel has a porosity which precludes the dialysate that filters through the holes 54 of the second conduit 36 from escaping into the bowel 18, but still permits the unconcentrated urine to permeate into the bowel 18, wherein the bowel functions to reabsorb water, electrolytes and small molecules resulting in concentrated urine.

Still referring to FIG. 5, it should be noted that in lieu of the relatively large holes 54 located in the second conduit 36 and the semi-permeable membrane 72 located within the bowel 18, the conduit 36 within the bowel 18 can be constructed like the central region 66 of the conduit 36 shown in FIG. 2. That is, in FIG. 5, the conduit 36 within the bowel 18 can be formed of the semi-permeable membrane.

As noted earlier, when the unconcentrated urine is turned into concentrated urine within the section of the patient's bowel 18, most of the concentrated urine will exit to the distal right ureter 24 which can be attached to the cecum or appendix 22 when appropriate. The concentrated urine will then flow into the urinary bladder 20 to be expelled intermediately, just as in a normally functioning human person. The dialysate and returning urine is returned through the distal end 46 of the conduit 36 into the abdominal region. Preferably, the distal end 46 of the second conduit 36 should either be of a very small diameter, or employ a moderate pressure one-way valve 48 therein to control the flow of fluid into the peritoneal space in a manner that allows adequate time for the bowel to absorb water from the unconcentrated urine passing therethrough, but not such as to prevent flow of unconcentrated or partially concentrated urine back into the peritoneal space for lymphatic reabsorption and recycling through the entire system.

It should be noted that the thoracic pouch 16 preferably communicates with a subcutaneous access reservoir 50, which includes an access section closely adjacent the patient's skin. The subcutaneous access reservoir 50 permits the monitoring and testing of the urine in order to determine the effectiveness of the prosthesis. The reservoir 50 also provides adjustments of urine flow and urine constituent by adding or subtracting dialysate to fit each patient's needs. The dialysate can be added or withdrawn from the subcutaneous access reservoir 50 using a syringe or tube inserted through the patient's skin into the reservoir.

Figure 6:
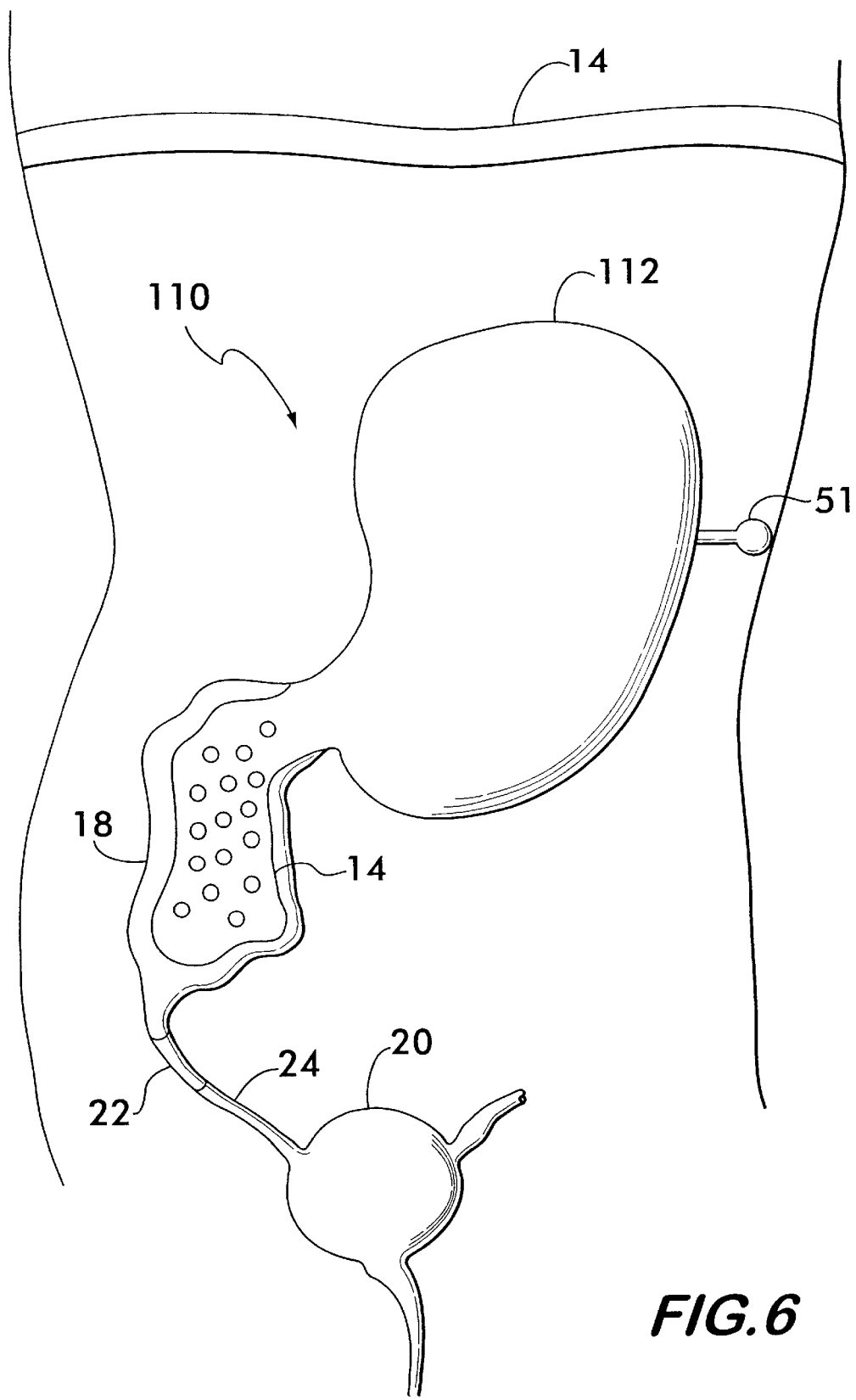
FIG. 6 is a front view of an internal peritoneal dialysis prosthesis of a sixth embodiment of the present invention showing parts thereof in section and being located in a person's body.

Referring to FIG. 6, there is shown at 110 an exemplary internal peritoneal dialysis prosthesis inserted within a patient's body in accordance with yet still another preferred embodiment of this invention. As shown in FIG. 6, the prosthesis 110 includes an abdominal sac 112 in the abdominal region of the patient below the diaphragm. The abdominal sac 112 includes an extension that expands into a section of the patient's bowel 18.

The abdominal sac 112 may be similar to the abdominal sacs discussed above. For example, the abdominal sac is arranged for having a dialysate therein. This sac 112 is generally formed of a semi-permeable membrane having a porosity which precludes the dialysate within the abdominal sac 112 from escaping into the peritoneal region but still permits unconcentrated urine within the peritoneal region to enter the abdominal sac 112 through osmotic pressure. Because the abdominal sac 112 is required to function in an aqueous environment, it preferably is formed of a synthetic plastic material with some elastic qualities (e.g., Gortex-like cloth). However, the abdominal sac 112 should not be so elastic as to expand to an extent that permits the dialysate molecules or microstructures to exit from expanded pores of its walls.

As with the abdominal sacs discussed above, portions of the wall of the abdominal sacs 112 may alternatively be formed of an impermeable or substantially impermeable membrane that is more elastic than the semi-permeable membrane and does not permit the dialysate to exit, even when the impermeable or substantially impermeable membrane is expanded beyond its elastic limit. Therefore, before the semi-permeable membrane expands under pressure to an extent that could permit dialysate to exit, the impermeable or substantially impermeable membrane stretches to contain the dialysate while inhibiting the dialysate from exiting therefrom.

Still referring to FIG. 6, a section of the patient's bowel 18 is sutured to the abdominal sac 112, thereby enclosing the extension 114 of the sac in the bowel. This extension includes the semi-permeable membrane wall so as to allow the unconcentrated urine drawn into the abdominal sac 112 by osmotic pressure to move into the bowel 18, wherein the bowel functions to reabsorb water, electrolytes and small molecules, resulting in concentrated urine. However, the semi-permeable membrane wall prevents the dialysate from moving into the bowel, thus keeping the dialysate within the abdominal sac 112.

The abdominal sac 112 preferably communicates with a subcutaneous access reservoir 51, which includes an access section closely adjacent the patient's skin. The subcutaneous access reservoir (SAR) 51 permits the monitoring and testing of the dialysate and urine in order to determine the effectiveness of the prosthesis. The SAR 51 provides adjustment of urine flow and urine constituents by adding or subtracting dialysate to fit each patient's needs. The dialysate can be added or withdrawn from the SAR 51 using a syringe or tube inserted through the patient's skin into the reservoir.

Unlike the other embodiments of the invention discussed above, the prosthesis 110 does not include conduits for continuous mixing and circulation of unconcentrated urine and dialysate. In this regard, it should be noted that the prosthesis 110 is likely not as efficient as the other preferred embodiments because this prosthesis 110 does not take advantage of a respiratory pump. Accordingly, this prosthesis is better suited for patients having a less severe renal failure. Another possible disadvantage of this embodiment is that the abdominal sac 112 may be subject to layering and stagnation of dialysate and receive unconcentrated urine making the patient more susceptible to infection. In other words, the mixing and circulation provided by the prosthesis of the embodiments discussed above improves the efficiency of the dialysis and precludes layering and stagnation of fluids within the prosthesis. The possible layering and stagnation of the fluids may be minimized in this embodiment if the patient frequently moves or changes the angular orientation (e.g., vertical, horizontal) of their torso, to allow the fluids in the abdominal sac 112 to flow influenced by gravitational pull. However, one advantage of this prosthesis over the embodiments described above, is that this prosthesis 110 uses fewer elements and is more simple in its operation. This prosthesis 110 also creates less strain on the patient during surgery to implant the prosthesis than the prosthesis of other preferred embodiments since fewer elements are inserted into the body.

It should be apparent from the aforementioned description and attached drawings that the concept of the present application may be readily applied to a variety of preferred embodiments, including those disclosed herein. For example, in FIG. 3. the distal end 46 of the second conduit 36 may include relatively large holes so as to allow unconcentrated urine and dialysis in the peritoneum to flow into the conduit 36 and the abdominal sac 64. Likewise, In FIG. 2, the central section 66 of the second conduit 36 has a semi-permeable wall, and can also include relatively large holes 54, as shown in the bowel 18 of FIG. 3. Similarly, in lieu of the relatively large holes 54 located in the second conduit 36 and the semi-permeable membrane 72 within the bowel 18 of FIG. 3, the conduit 36 within the bowel 18 can be constructed like the central region 66 of the conduit 36 shown in FIG. 2. That is, in FIG. 3, the conduit 36 within the bowel 18 can be formed of a semi-permeable membrane. Moreover, in FIG. 4, instead of coupling the distal end of the second conduit to the dialysis sac 84, the distal end may extend to and end in the peritoneal space to return a percentage of the fluid to the peritoneum. In this example the distal end 46 of the conduit 36 should either be of a very small diameter, or employ a moderate pressure one-way valve 46 therein to control the flow of fluid into the peritoneal space in a manner that allows adequate residence time for the bowel to absorb water from the unconcentrated urine passing therethrough, but not such as to prevent flow of partially concentrated urine into the peritoneal space for lymphatic reabsorption and recycling through the entire system. In addition, the ureter 24 could be connected directly to the bowel 18, thus bypassing the appendix 22. In this preferred embodiment, the appendix 22 would not be used.

Without further elaboration the foregoing will so fully illustrate my invention that others may, by applying current or future knowledge, readily adapt the same for use under various conditions of service.

What is claimed is:

1. A prosthesis for continuous internal peritoneal dialysis, comprising:

a first conduit adapted to continuously communicate unconcentrated urine from the abdominal region of a patient's body from outside said prosthesis into said first conduit and through the patient's diaphragm to the thoracic region of the body;

a thoracic pouch adapted to be retained in the thoracic region of a patient's body, said thoracic pouch communicating with said first conduit to receive the unconcentrated urine from the abdominal region; and a second conduit adapted to communicate the unconcentrated urine from said thoracic pouch through the patient's diaphragm, said second conduit adapted to extend through a section of the patient's bowel separated from the digestion system of the patient, a region of said second conduit within the section of the patient's bowel adapted to communicate the unconcentrated urine in said second conduit within walls of the section of bowel for concentrating said urine within the section of bowel.

2. The prosthesis of claim 1 wherein said region of said second conduit within said section of the patient's bowel includes apertures for communicating the unconcentrated urine in said conduit with said walls of said section of bowel.

3. The prosthesis of claim 2, wherein said second conduit includes a distal end downstream of the apertures and communicating with the abdominal region, said distal end communicating the unconcentrated urine and dialysate from the region of said second conduit within said section of the patient's bowel into the abdominal region.

4. The prosthesis of claim 1 wherein said region of said second conduit within said section of the patient's bowel includes a semi-permeable membrane having a porosity which permits unconcentrated urine to pass through said conduit into the section of bowel and which precludes the dialysate from exiting said conduit to said walls of said section of bowel.

5. The prosthesis of claim 1 further comprising connecting means for directing the concentrated urine from said section of bowel to the urinary bladder of the patient.

6. The prosthesis of claim 5, wherein said connecting means includes the right ureter connecting the bowel to the urinary bladder.

7. The prosthesis of claim 6, wherein said connecting means includes the appendix or cecum connecting the bowel to the right ureter.

8. The prosthesis of claim 1, wherein said first conduit includes apertures for receiving unconcentrated urine from the abdominal region.

9. The prosthesis of claim 8, wherein said apertures of said first conduit also receive dialysate from the peritoneum.

10. The prosthesis of claim 1, wherein said first conduit includes a one way valve for permitting the unconcentrated urine to flow only in a direction from said abdominal region towards said thoracic pouch.

11. The prosthesis of claim 1, wherein said second conduit includes a one way valve between said thoracic pouch and said section of the patient's bowel for permitting the unconcentrated urine to flow only in a direction from said pouch towards said section.

12. The prosthesis of claim 1, further comprising a subcutaneous access reservoir substantially adjacent the patient's skin, the subcutaneous access reservoir in communication with said thoracic pouch for monitoring and adjusting unconcentrated urine flow and constituents.

13. The prosthesis of claim 1, said section of bowel including an exit port adapted to direct the concentrated urine from said section of bowel to the urinary bladder of the patient.

14. The prosthesis of claim 1, further comprising an abdominal sac adapted for internal peritoneal dialysis, said sac including a semi-permeable membrane wall and arranged for having a dialysate therein, said sac adapted to be retained in the abdominal region for receiving unconcentrated urine through said semi-permeable membrane wall, the dialysate exerting chemical potential to draw in the unconcentrated urine through said semi-permeable membrane wall, said sac communicating the unconcentrated urine from said sac to said first conduit.

15. The prosthesis of claim 14, wherein said second conduit includes a one way valve at said distal end for permitting the unconcentrated urine to flow only in a direction from said section of the patient's bowel towards said abdominal sac.

16. The prosthesis of claim 14, wherein said second conduit communicates urine to said abdominal sac.

17. The abdominal sac of claim 14, further comprising a subcutaneous access reservoir substantially adjacent the patient's skin, the subcutaneous access reservoir being in communication with said sac for adding dialysate to or withdrawing dialysate from said sac.

* * * * *